United States Patent [19]

Combourieu et al.

[11] Patent Number: 5,238,939

[45] Date of Patent: Aug. 24, 1993

[54] ISOCHROMANE DERIVATIVES

[75] Inventors: Michel Combourieu, Cebazat; Jean-Claude Laigle; Nadine Simbille, both of Riom, all of France

[73] Assignee: Akzo N.V., Arnhem, Netherlands

[21] Appl. No.: 887,578

[22] Filed: May 19, 1992

Related U.S. Application Data

[63] Continuation of Ser. No. 703,974, May 22, 1991, abandoned.

[30] Foreign Application Priority Data

May 25, 1990 [EP] European Pat. Off. ........ 90401407.3

[51] Int. Cl.$^5$ .................. C07D 405/06; C07D 405/04; C07D 493/04; A61K 31/495
[52] U.S. Cl. .................................. 514/253; 544/376; 544/378
[58] Field of Search ................. 514/253; 544/376, 378

[56] References Cited

U.S. PATENT DOCUMENTS 4,066,648 1/1978 Oka ..................................... 544/402

FOREIGN PATENT DOCUMENTS 1552004 5/1976 United Kingdom .

Primary Examiner—Mark L. Berch
Attorney, Agent, or Firm—William M. Blackstone

[57] ABSTRACT

The invention concerns an isochromane derivative having the general formula I

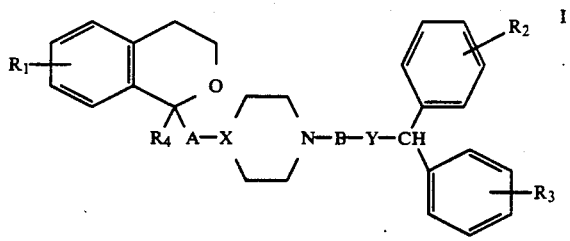

in which $R_1$ is one to four substituents independently selected from hydrogen, hydroxy, alkyl (1–4 C), alkoxy (1–4 C), halogen, or $CF_3$, or as two adjacent substituents together a methylenedioxy group;

$R_2$ is one to four substituents independently selected from hydrogen, hydroxy, alkyl (1–4 C), alkoxy (1–4 C), halogen, or $CF_3$, or as two adjacent substituents together a methylenedioxy group;

$R_3$ is one to four substituents independently selected from hydrogen, hydroxy, alkyl (1–4 C), alkoxy (1–4 C), halogen, or $CF_3$, or as two adjacent substituents together a methylenedioxy group;

$R_4$ is selected from hydrogen or alkyl (1–4 C);

A is a bond or an alkylene or alkylidene group with 1-6 carbon atoms;

B is an alkylene or alkylidene group with 1-6 carbon atoms when Y is a bond, or B is an alkylene group with 2-6 carbon atoms when Y is a group selected from O, S, or $NR_5$;

X is CH or N; and $R_5$ is selected from hydrogen or alkyl (1–4 C); or a pharmaceutically acceptable salt thereof.

The compounds can be used in the treatment of angina pectoris, cardiac dysrhytmias, cardiomyopathies, stroke, and myocardial infarction.

6 Claims, 1 Drawing Sheet

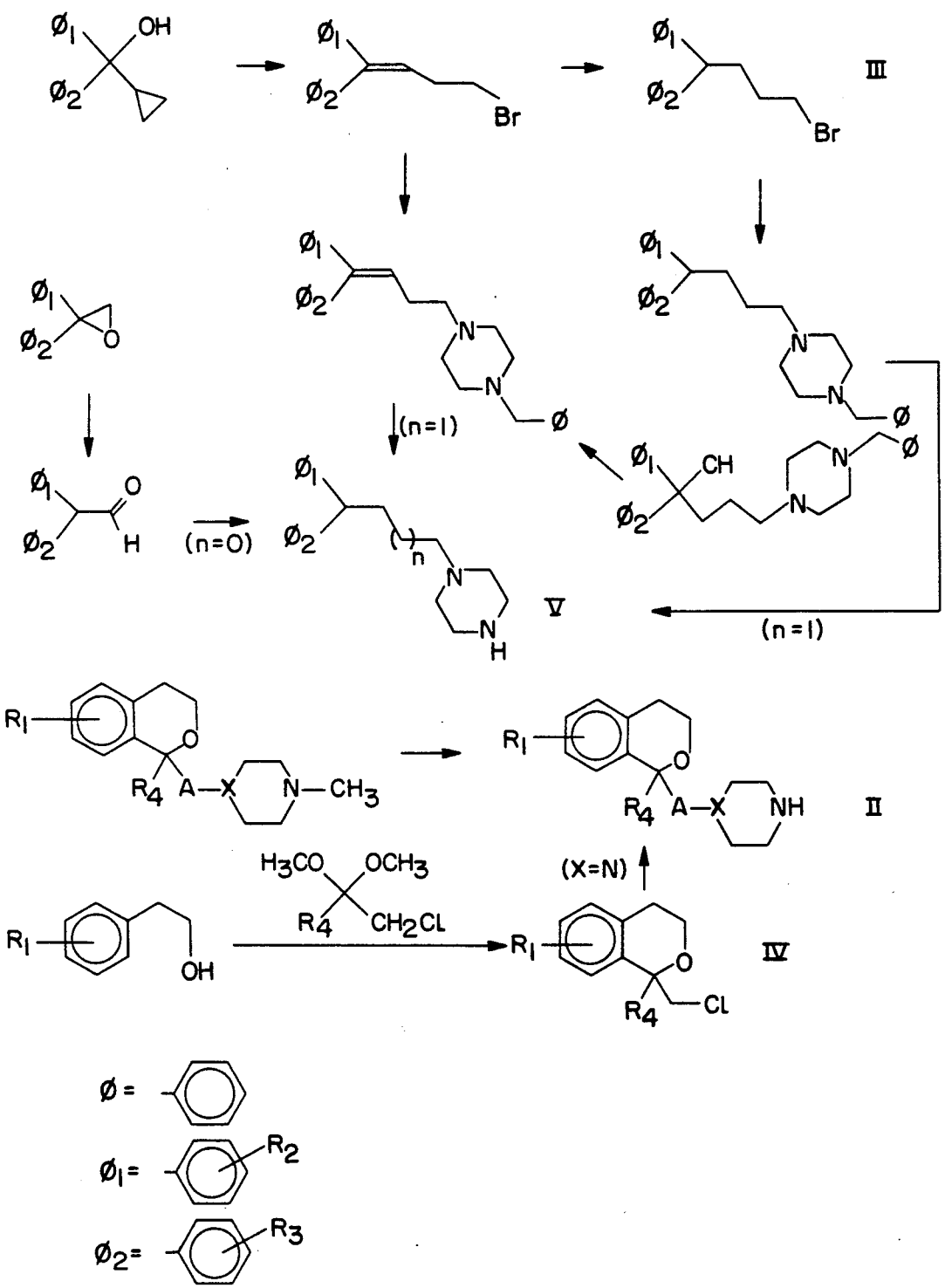

ISOCHROMANE DERIVATIVES

This is a continuation of application Ser. No. 07/703,974 filed May 22, 1991 abandoned.

The invention concerns isochromane derivatives, their processes for preparation and pharmaceutical compositions containing the same. The compounds of the invention have the general formula I

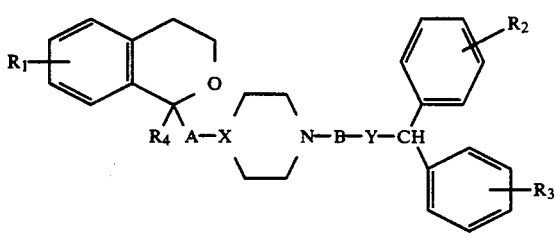

in which $R_1$ is one to four substituents independently selected from hydrogen, hydroxy, alkyl (1–4 C), alkoxy (1–4 C), halogen, or $CF_3$, or as two adjacent substituents together a methylenedioxy group;

$R_2$ is one to four substituents independently selected from hydrogen, hydroxy, alkyl (1–4 C), alkoxy (1–4 C), halogen, or $CF_3$, or as two adjacent substituents together a methylenedioxy group;

$R_3$ is one to four substituents independently selected from hydrogen, hydroxy, alkyl (1–4 C), alkoxy (1–4 C), halogen, or $CF_3$, or as two adjacent substituents together a methylenedioxy group;

$R_4$ is selected from hydrogen or alkyl (1–4 C);

A is a bond or an alkylene or alkylidene group with 1–6 carbon atoms;

B is an alkylene or alkylidene group with 1–6 carbon atoms when Y is a bond, or B is an alkylene group with 2–6 carbon atoms when Y is a group selected from O, S, or $NR_5$;

X is CH or N; and $R_5$ is selected from hydrogen or alkyl (1–4 C); or a pharmaceutically acceptable salt thereof.

The compounds of this invention are potent intracellular calcium antagonists, which inhibit contractile responses induced by $Ca^{++}$ channel activation, $Ca^{++}$ release process triggered by a variety of agonists, as well as $Ca^{++}$ uptake induced by depolarisation in brain slices, and can be used in the treatment of angina pectoris, cardiac dysrhytmias, or cardiomyopathies. The compounds are also strong inhibitors of blood platelet aggregation, and therefore suitable drugs for the treatment of stroke, or myocardial infarction.

The term halogen used in the definition of formula I means fluorine, chlorine, bromine or iodine. Fluorine is the preferred halogen. The term alkyl (1–4 C) means a branched or unbranched alkyl group with 1–4 carbon atoms, such as methyl, ethyl, propyl, isopropyl, butyl, and tert-butyl. The alkyl moiety which is present in the alkoxy (1–4 C) group has the same meaning as previously defined for alkyl (1–4 C). The alkylene or alkylidene group is a saturated branched or unbranched aliphatic alkylene or alkylidene group with 1 to 6 carbon atoms. Examples of alkylene groups are methylene, 1,2-ethanediyl, 1,3-propanediyl, 1,4-butanediyl, and 1-methyl-1,2-ethanediyl. Examples of alkylidene groups are ethylidene and propylidene. Preferred are unbranched alkylene groups with 1 to 4 carbon atoms. Most preferred are the methylene, 1,2-ethanediyl, and 1,3-propanediyl groups. The alkylene groups with 2 to 6 carbon atoms have the same definition as the alkylene groups with 1 to 6 carbon atoms, but with the exclusion of the methylene group.

Preferred isochromane derivatives according to the invention have formula I, in which $R_1$ represents one, two or three methoxy groups, or a methylenedioxy group, $R_2$ and $R_3$ are hydrogen or halogen, $R_4$ is selected from hydrogen, methyl, or ethyl, A is methylene or 1,2-ethanediyl, B is 1,2-ethanediyl or 1,3-propanediyl, Y is a bond, O, or S, and X is N; or a pharmaceutically acceptable salt thereof.

Other preferred isochromane derivatives according to the invention have formula I, in which $R_1$ represents one, two or three methoxy groups, or a methylenedioxy group, $R_2$ and $R_3$ are hydrogen or halogen, $R_4$ is methyl, A is a bond, B is 1,2-ethanediyl or 1,3-propanediyl, Y is a bond or O; and X is CH; or a pharmaceutically acceptable salt thereof.

Of the preferred isochromane derivatives, more specifically are mentioned the derivatives in which $R_2$ and $R_3$ are hydrogen or para-fluorine.

The most preferred compounds are the isochromane derivatives having the formulas

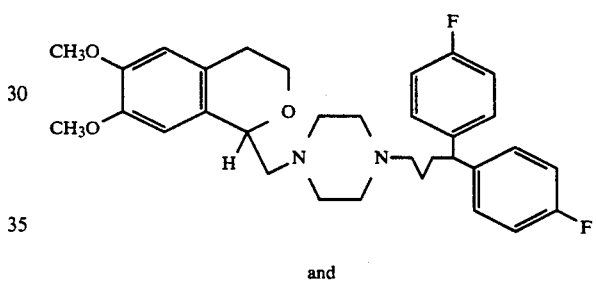

and

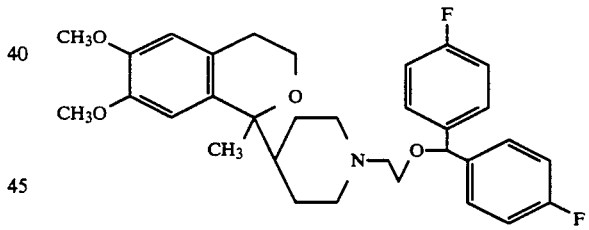

or a pharmaceutically acceptable salt thereof.

The novel compounds of formula I may be isolated from a reaction mixture in the form of a pharmaceutically acceptable salt. The pharmaceutically acceptable salts may also be obtained by treating the free base of formula I with an organic or inorganic acid such as HCl, HBr, HI, $H_2SO_4$, $H_3PO_4$, acetic acid, propionic acid, glycolic acid, maleic acid, malonic acid, methanesulphonic acid, fumaric acid, succinic acid, tartaric acid, citric acid, benzoic acid, and ascorbic acid.

The compounds of this invention possess one or more chiral carbon atoms, and may therefore be obtained as a pure enantiomer, or as a mixture of enantiomers, among which the racemic mixture. Methods for obtaining the pure enantiomers are well known in the art, e.g. synthesis with chiral induction, crystallization of salts which are obtained from optically active acids and the racemic mixture, or chromatography using chiral columns.

The compounds of the invention may be prepared by methods in use for analogous compounds. A suitable method, for instance, is the condensation of compound II with compound III,

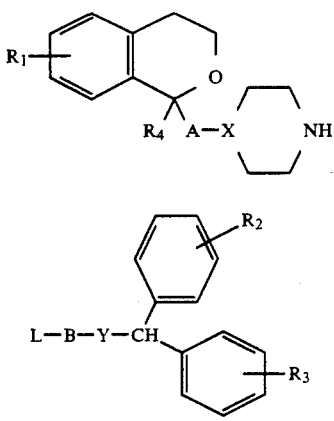

in which $R_1$-$R_4$, X, Y, A and B have the previously given meanings, and L is a leaving group. The leaving group is a group commonly used as leaving group, such as a mesylate or tosylate group, or a halogen, such as chlorine or bromine.

Compounds with X is N can also be prepared by the condensation of compound IV with compound V

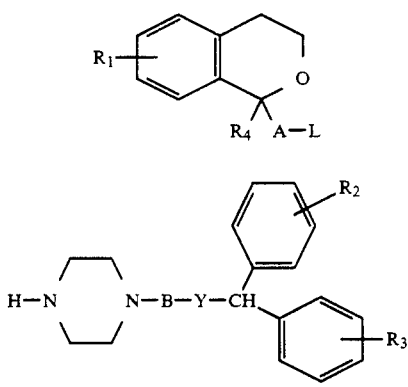

in which $R_1$-$R_4$, Y, A, B and L have the previously given meanings.

Starting products II–V are easily available according to methods generally known in organic chemistry. Some approaches for the preparation of compounds II–V are, as an example, depicted in the FIGURE.

The FIGURE illustrates in schematic form pathways for synthesizing compounds II–V from conventionally available starting materials using methods known in the art.

It is possible to convert the products obtained by one of the previously mentioned procedures into another product according to the invention. Using generally known methods it is, for instance, possible to convert aromatic substituents into other aromatic substituents. Hydroxy substituted compounds may be condensed with lower alcohols in acidic medium to give alkoxy derivatives, and ortho-dihydroxy substituted compounds may be condensed with formaldehyde to give methylenedioxy substituted derivatives. Compounds wherein $R_5$ is hydrogen may be alkylated, e.g. by a Leuckart-Wallach reaction, to afford compounds wherein $R_5$ is alkyl.

The compounds of the invention may be administered enterally or parenterally, and for humans preferably in a daily dosage of 0,01–50 mg per kg body weight. Mixed with pharmaceutically suitable auxiliaries, e.g. as described in the standard reference, Chase et al., Remington's Pharmaceutical Sciences, the compounds may be compressed into solid dosage units, such as pills, tablets, or be processed into capsules or suppositories. By means of pharmaceutically suitable liquids the compounds can also be applied as an injection preparation in the form of a solution, suspension, emulsion, or as a spray, e.g. a nasal spray. The invention is illustrated by the following examples.

EXAMPLE 1

1-[2-(1-ethyl-3,4-dihydro-6,7-dimethoxy-1H-2-benzopyran-1-yl) ethyl]-4-(4,4-diphenylbutyl)-piperazine (E)-2-butenedioate (1:2) salt a. A mixture of 26,5 g of α-cyclopropyl-α-phenylbenzenemethanol and 150 ml of 48% HBr was stirred at ambient temperature for 3 h. After addition of icewater, the mixture was extracted twice with diethyl ether, washed, dried and concentrated to obtain 33 g (97,3%) of 4-bromo-1,1-diphenyl-1-butene.

b. A mixture of 33 g of 4-bromo-1,1-diphenyl-1-butene, 15,6 g of 1-(phenylmethyl)piperazine, 15,9 g of potassium carbonate and 200 ml of dimethylformamide was heated at 110° C. for 2 h. After hydrolysis with water the mixture was extracted with diethyl ether, dried and concentrated. The residue was dissolved in absolute ethanol in which 38,6 g (96,6%) of 1-(4,4-diphenyl-3-butenyl)-4-(phenylmethyl)piperazine hydrochloride was precipitated by anhydrous hydrochloric acid.

c. A mixture of 38,6 g of 1-(4,4-diphenyl-3-butenyl)-4-(phenylmethyl)piperazine hydrochloride and 4 g of 5% Pd on activated charcoal in a minimal amount of methanol was hydrogenated under 50 psi for 1 h. After filtration of the catalyst the methanol was evaporated and replaced by ethanol after which 26,1 g (85,5%) of (4,4-diphenylbutyl)piperazine hydrochloride precipitated.

d. A mixture of 8 g of 1-(4,4-diphenylbutyl)piperazine hydrochloride, 8,4 g of known 1-(2-chloroethyl)-1-ethyl-3,4-dihydro-6,7-dimethoxy-1H-2-benzopyran, 5,6 g of potassium carbonate and 1 g of potassium iodide in 100 ml of dimethylformamide was heated at 100° C. for 3 h. After hydrolysis the mixture was extracted twice with ethyl acetate, dried and concentrated. The difumarate salt was prepared by adding 14,6 g of fumaric acid to a solution of the free base in ethanol, to give 4,2 g (35,6%) of 1-[2-(1-ethyl-3,4-dihydro-6,7-dimethoxy-1H-2-benzopyran-1-yl)ethyl]-4-(4,4-diphenylbutyl)piperazine (E)-2-butenedioate (1:2) salt. mp 207,8° C.

EXAMPLE 2

1-[2-(1-ethyl-3,4-dihydro-6.7-dimethoxy-1H-2-benzopyran-1-yl)ethyl -4-[4,4-bis(4-fluorophenyl)butyl]-piperazine (Z)-2-butenedioate (1:2) salt a. A mixture of 30,5 g of 1-chloro-3-pentanone, 25 g of 1-methylpiperazine, 41,9 g of potassium carbonate and 400 ml of acetone was refluxed for 3 h. The mixture was filtered and the acetone was evaporated. The residue was dissolved in aqueous hydrochloric acid and the resulting solution was washed twice with diethyl ether.

The aqueous phase was basified with potassium carbonate and extracted twice with dichloromethane. The organic phase was washed, dried and evaporated to yield 33,8 g (73,3%) of crude 1-(4-methylpiperazinyl)-pentane-3-one.

b. A mixture of 34,8 g of 3,4-dimethoxybenzeneethanol and 32 g of crude 1-(4-methylpiperazinyl)pentane-3-one in 400 ml of dioxane, which is saturated with anhydrous hydrochloric acid, was stirred at ambient temperature for 24 h. After addition of water the mixture was extracted with dichloromethane. The organic phase was washed, dried and evaporated to yield 41,5 g (68,5%) of crude 1-[2-(1-ethyl-3,4-dihydro-6,7-dimethoxy-1H-2-benzopyran-1-yl)ethyl]-4-methylpiperazine.

c. A mixture of 20 g of crude 1-[2-(1-ethyl-3,4-dihydro-6,7-dimethoxy-1H-2-benzopyran-1-yl)ethyl]-4-methylpiperazine and 7,5 g of phenylchloroformate in 150 ml of toluene was refluxed for 4 h. The toluene was evaporated, and the residue dissolved in a mixture of 150 ml of ethanol and 150 ml of 50% aqueous sodium hydroxide and refluxed for 2 h. The ethanol was evaporated and the residue dissolved in diethyl ether. The solution was washed, dried and concentrated and the residue was dissolved in acetone with anhydrous hydrochloric acid to yield 20,4 g (87,9%) of crude 1-[2-(1-ethyl-3,4-dihydro-6,7-dimethoxy-1H-2-benzopyran-1-yl)ethyl]piperazine dihydrochloride.

d. A mixture of 6,2 g of crude 1-[2-(1-ethyl-3,4-dihydro-6,7-dimethoxy-1H-2-benzopyran-1-yl)ethyl]piperazine dihydrochloride, 6,8 g of 1,1-bis(4-fluorophenyl)-4-chlorobutane, 6,6 g of potassium carbonate and 2,9 g of potassiun iodide in 200 ml of dimethylformamide was heated at 100° C. for 2 h. After hydrolysis the mixture was extracted with a mixture of diethyl ether and ethyl acetate. After drying and evaporation the dimaleate was prepared in absolute ethanol to give 8 g (54,8%) of 1-[2-(1-ethyl-3,4-dihydro-6,7-dimethoxy-1H-2-benzopyran-1-yl)ethyl]-4-[4,4-bis(4-fluorophenyl)butyl]-piperazine (Z)-2-butenedioate (1:2) salt. mp 175° C.

EXAMPLE 3

In an analogous manner as described in Example 2 were prepared:

1-[2-(1-ethyl-3,4-dihydro-6,7-dimethoxy-1H-2-benzopyran-1-yl)ethyl]-4-[2-[bis(4-fluorophenyl)methoxy]ethyl]-piperazine (Z)-2-butenedioate (1:2) salt. mp 174° C.

1-[2-(1-ethyl-3,4-dihydro-6,7-dimethoxy-1H-2-benzopyran-1-yl)ethyl]-4-[2-(diphenylmethoxy)ethyl]piperazine (Z)-2-butenedioate (1:2) salt. mp 165° C.

1-[2-(1-ethyl-3,4-dihydro-6,7-dimethoxy-1H-2-benzopyran-1-yl)ethyl]-4-[2-[bis(4-fluorophenyl)methylthio]ethyl]-piperazine (Z)-2-butenedioate (1:2) salt. mp 177° C.

EXAMPLE 4

1-[2-(1-ethyl-3.4-dihydro-6-methoxy-1H-2-benzopyran-1-yl)ethyl]-4-4,4-bis(4-fluorophenyl)butyl]piperazine Z)-2-butenedioate (1:2) salt A mixture of 7,6 g of known 1-(2-chloroethyl)-1-ethyl-3,4-dihydro-6-methoxy-1H-2-benzopyran, 9 g of 1-[4,4-bis(4-fluorophenyl)butyl]piperazine, 0,4 g of potassium iodide, and 5 g of potassium carbonate in 100 ml of dimethylformamide was refluxed for 6 h. After hydrolysis the mixture was extracted with dimethyl ether, and the ethereal phase was washed, dried, and evaporated. The base was precipitated and the dimaleate salt was prepared in ethanol and recrystallized from ethanol-water (3:1) to give 13,8 g of 1-[2-(1-ethyl-3,4-dihydro-6-methoxy-1H-2-benzopyran-1-yl)ethyl]-4-[4,4-bis(4-fluorophenyl)butyl]piperazine (Z)-2-butenedioate (1:2) salt. mp 184° C.

EXAMPLE 5

In an analogous manner as described in Example 4 were prepared:

1-[2-(1-ethyl-3,4-dihydro-5,6-dimethoxy-1H-2-benzopyran-1-yl)ethyl]-4-[4,4-bis(4-fluorophenyl)butyl]piperazine (Z)-2-butenedioate (1:2) salt. mp 180° C.

1-[2-(1-ethyl-3,4-dihydro-6,7,8-trimethoxy-1H-2-benzopyran-1-yl)ethyl]-4-[4,4-bis(4-fluorophenyl)butyl]-piperazine (Z)-2-butenedioate (1:2) salt. mp 217° C.

1-[2-(1-ethyl-3,4-dihydro-6,7-methylenedioxy-1H-2-benzopyran-1-yl)ethyl]-4-[4,4-bis(4-fluorophenyl)-butyl]-piperazine (Z)-2-butenedioate (1:2) salt. mp 284° C.

EXAMPLE 6

1-[4,4-bis(4-fluorophenyl)butyl]-4-(3,4-dihydro-6,7-dimethoxy-1H-2-benzopyran-1-yl)methyl]piperazine (Z)-2-butenedioate (1:2) salt a. A mixture of 3,4-dimethoxybenzeneethanol and 62,8 g of chloroacetaldehyde diethylacetal in 1 l of absolute ethanol saturated with anhydrous hydrochloric acid, was stirred at ambient temperature for 24 h. The solvent was evaporated and 88,4 g (88,8%) of 1-chloromethyl-3,4-dihydro-6,7-dimethoxy-1H-2-benzopyran was obtained by distillation.

b. A mixture of 88 g of 1-chloromethyl-3,4-dihydro-6,7-dimethoxy-1H-2-benzopyran, 76,7 g of 1-(phenylmethyl)piperazine, 74,6 g of potassium carbonate and 10 g of potassium iodide in 1 l of dimethylsulfoxide was heated at 80° C. for 3 h. After addtion of water the mixture was extracted with ethyl acetate, and the organic phase was washed, dried and evaporated. By precipitation under diisopropyl ether 53,5 g (38,8%) of 1-[(3,4-dihydro-6,7-dimethoxy-1H-2-benzopyran-1-yl)methyl]-4-(phenylmethyl)piperazine was obtained.

c. A mixture of 53 g of 1-[(3,4-dihydro-6,7-dimethoxy-1H-2-benzopyran-1-yl)methyl]-4-(phenylmethyl)piperazine, 150 ml of methanol, 150 ml of water and 5 g of 5% Pd on activated charcoal was acidified with 36% hydrochloric acid and hydrogenated at 50 psi until absorption of hydrogen was finished. The catalyst was filtered and the solvent evaporated, after which the residue was basified with sodium hydroxide and extracted with dichloromethane. The dichloromethane phase was washed, dried and evaporated and the product precipitated under diisopropyl ether to obtain 1-[(3,4-dihydro-6,7-dimethoxy-1H-2-benzopyran-1-yl)methyl]piperazine.

d. A mixture of 8 g of 1-[(3,4-dihydro-6,7-dimethoxy-1H-2-benzopyran-1-yl)methyl]-4-(phenylmethyl)piperazine, 9,1 g of 1,1-bis(4-fluorophenyl)-4-chlorobutane and 5,6 g of potassium carbonate in 75 ml of dimethylformamide was heated at 90° C. for 2 h. After addition of water the mixture was extracted with diethyl ether, the ether phase was washed, dried and evaporated and the dimaleate prepared as previously described to obtain 5,3 g (36,5%) of 1-[4,4-bis(4-fluorophenyl)butyl]-4-[(3,4-dihydro-6,7-dimethoxy-1H-2-benzopyran-1-yl)methyl]piperazine (Z)-2-butene-dioate (1:2) salt. mp 205° C.

EXAMPLE 7

In an analogous manner as described in Example 6 was prepared:

1-[2-[bis(4-fluorophenyl)methoxy]ethyl]-4-[(3,4-dihydro-6,7-dimethoxy-1H-2-benzopyran-1-yl)methyl]piperazine (E)-2-butenedioate (1:2) salt. mp 201° C.

1-[(3,4-dihydro-6,7-dimethoxy-1H-2-benzopyran-1-yl)-methyl]-4-(4,4-diphenylbutyl)-piperazine (Z)-2-butene-dioate (1:2) salt. mp 202° C.

EXAMPLE 8

1-[2-(1-ethyl-3,4-dihydro-6,7-dimethoxy-1H-2-benzopyran-1-yl)ethyl]-4-[3.3-bis(4-fluorophenyl)propyl]-piperazine(E)-2-butenedioate (1:2) salt a. A mixture of 54 g of 1-(4-fluorophenyl)ethanone, 39,1 g of dimethylamine hydrochloride, 14,4 g of paraformaldehyde, and 10 ml of 36% hydrochloric acid was refluxed for 2 h in 500 ml of ethanol. The ethanol was evaporated and ethyl acetate was added, after which 79 g (82%) of 1-(4-fluorophenyl)-3-(dimethyl-amino)-propanone hydrochloride was obtained.

b. A mixture of 75 g of 1-(4-fluorophenyl)-3-(dimethyl-amino)-propanone hydrochloride and 62,8 g of 1-(phenylmethyl)piperazine in 300 ml of toluene was refluxed for 8 h. The solvent was evaporated and the residue was washed with diethyl ether, diluted with sodium hydroxide and water. The residue was then dried by adding toluene and evaporation of the solvent, to yield 84,4 g (79,8%) of 1-(4-fluoro-phenyl)-3-[4-(phenylmethyl)-1-piperazinyl]-1-propan-one hydrochloride.

c. To a Grignard reagent, which was prepared from 6,3 g of magnesium and 45 g of 1-bromo-4-fluorobenzene in tetrahydrofuran, was added cautiously 70 g of 1-(4-fluorophenyl)-3-[4-(phenylmethyl)-1-piperazinyl])-1-propanone hydrochloride, and the mixture was refluxed for 2 h. The mixture was hydrolyzed with brine, the mineral salts were filtered and the solvent was evaporated. By addition of diisopropyl ether 28,8 g (31,9%) of 1,1-bis(4-fluorophenyl)-3-[4-(phenyl-methyl)-1-piperazinyl]-1-propanol was obtained.

d. A mixture of 28,8 g of 1,1-bis(4-fluorophenyl)-3-[4-(phenylmethyl)-1-piperazinyl])-1-propanol in 150 ml of ethanol saturated with hydrochloric acid was refluxed for 4 h. The solvent was evaporated and the residue was dissolved in absolute ethanol, to obtain 32,5 (100%) of 1-[3,3-bis(4-fluorophenyl)-2-propenyl]-4-(phenylmethyl)piperazine dihydrochloride.

e. A mixture of 32,5 g of 1-[3,3-bis(4-fluorophenyl)-2-propenyl]-4-(phenylmethyl)piperazine dihydrochloride and 3,3 g of 5% Pd at activated charcoal in 150 ml of methanol and 100 ml of water was hydrogenated under 60 psi. The catalyst was filtered off and after evaporation of the solvent basification with sodium hydroxide was achieved. The base was extracted with ethyl acetate and the organic phase was washed, dried and evaporated to yield 21,5 g (90,7%) of crude 1-[3,3-bis(4-fluorophenyl)propyl]piperazine.

f. A mixture of 8,6 of 1-(2-chloroethyl)-1-ethyl-3,4-dihydro-6,7-dimethoxy-1H-2-benzopyran, 8 g of 1-[3,3-bis(4-fluorophenyl)propyl]piperazine, 5,2 g of potassium carbonate and 0,4 g of potassium iodide in 100 ml of dimethylformamide was refluxed for 4 h. Water was added and the base was extracted twice with ethyl acetate. After washing, drying and evaporation the difumarate was prepared in absolute ethanol to yield 13,2 g (61,2%) of 1-[2-(1-ethyl-3,4-dihydro-6,7-dimethoxy-1H-2-benzopyran-1-yl)ethyl]-4-[3,3-bis-(4-fluorophenyl)-propyl]piperazine (E)-2-butenedioate (1:2) salt.

EXAMPLE 9

1-[2-(1-ethyl-3,4-dihydro-6,7-dimethoxy-1H-2-benzopyran-1-yl)ethyl]-4-[2,2-bis(4-fluorophenyl)ethyl]piperazine (Z)-2-butenedioate (1:2) salt a. A mixture of 7,9 g of sodium hydride and 72,6 g of trimethyl sulfoxonium iodide was stirred for 30 min in 200 ml of dimethylformamide at ambient temperature. Then 60 g of bis(4-fluorophenyl)methanone dissolved in dimethylsulfoxide was added progressively in 2 h. Stirring was continued 1 h at ambient temperature and the reaction product was extracted with ethyl acetate. After evaporation of the solvent 61,5 g (96,3%) of 2,2-bis(4-fluoro-phenyl)oxirane was obtained.

b. Under vigorous stirring 18,5 g of boron trifluoride etherate was added slowely to a solution of 60,6 g of 2,2-bis(4-fluorophenyl)oxirane in 450 ml of toluene. The mixture was washed twice with water, the solvent was evaporated and the residue was distilled to yield α-(4-fluorophenyl)-4-fluorobenzeneacetaldehyde.

c. A mixture of 31 g of α-(4-fluorophenyl)-4-fluorobenzeneacetaldehyde and 19,4 g of 1-(phenylmethyl)-piperazine was refluxed for 30 min in 150 ml of methanol. After cooling 10,4 g of sodium cyanoborohydride were added. After 30 min acetic acid was added until acidic pH. The methanol was evaporated and the residue treated by water and dichloromethane. The organic phase was washed, dried and evaporated, and the hydrochloride was prepared in ethanol to yield 41,6 g (81%) of 1-[2,2-bis(4-fluorophenyl)-ethyl]-4-(phenylmethyl)piperazine hydrochloride.

d. In an analogous manner as described in Example 6c 41 g of 1-[2,2-bis(4-fluorophenyl)ethyl]-4-(phenylmethyl)piperazine hydrochloride gave 20,9 g (78,6%) of 1-[2,2-bis(4-fluorophenyl)ethyl]piperazine.

e. In an analogous manner as described in Example 4, 1-[2-(1-ethyl-3,4-dihydro-6,7-dimethoxy-1H-2-benzopyran-1-yl)ethyl]-4-[2,2-bis(4-fluorophenyl)ethyl]-piperazine (Z)-2-butenedioate (1:2) salt in 70,6% yield was obtained. mp 179° C.

EXAMPLE 10

Starting from the racemic product of Example 2, the separation of the enantiomers was achieved by using D(−)-2,3-dihydroxy-1,4-butenedioate and L(+)-2,3-dihydroxy-1,4-butenedioate. The two acids led respectively, after four crystallizations, to pure enantiomers (purity >95%). The bases were regenerated and dimaleates were prepared as for the racemates, to obtain:

(−)-1-[2-(1-ethyl-3,4-dihydro-6,7-dimethoxy-1H-2-benzopyran-1-yl)ethyl]-4-[4,4-bis(4-fluorophenyl)-butyl]piperazine (Z)-2-butenedioate (1:2) salt. mp 189° C.; $[\alpha]_D^{20} = -14,5°$ (+)-1-[2-(1-ethyl-3,4-dihydro-6,7-dimethoxy-1H-2-benzopyran-1-yl)ethyl]-4-[4,4-bis(4-fluorophenyl)-butyl]piperazine (Z)-2-butenedioate (1:2) salt. mp 187° C.; $[\alpha]_D^{20} = +13,2°$

EXAMPLE 11

(+)-1-[4,4-bis(4-fluorophenyl)butyl]-4-[(3,4-dihydro-6,7-dimethoxy-1H-2-benzopyran-1-yl)methyl]piperazine (Z)-2-butenedioate (1:2) salt To a hot mixture of 60 g of 1-[(3,4-dihydro-6,7-dimethoxy-1H-2-benzopyran-1-yl)methyl]-4-phenylmethylpiperazine in 400 ml of ethanol was added 63,4 g of (+)-di-O,O'-p-toluoyltartaric acid. The mixture was slowely cooled down and after 12 h standing at ambient temperature, the precipitate was filtered, washed with ethanol, and recrystallized from 300 ml of ethanol to give 54,4 g of enantiomeric pure salt. The base was freed, and from 24 g of free base, 14,4 g of (+)-1-[(3,4-dihydro-6,7-dimethoxy-1H-2-benzopyran-1-yl)methyl]-piperazine having an enantiomeric purity >98% were obtained after hydrogenation with 5% Pd on charcoal, as described in Example 6c. 14,2 g Of (+)-1-[(3,4-dihydro-6,7-dimethoxy-1H-2-benzopyran-1-yl)methyl]-piperazine were reacted with 13,6 g of 1,1-bis(4-fluorophenyl)-4-chlorobutane and 8 g of potassium carbonate in 100 ml of dimethyl formamide for 2 h. Water was added to the mixture and after workup, the dimaleate was prepared as previously described to obtain 11,4 g of (+)-1-[4,4-bis(4-fluorophenyl)-butyl-4-[(3,4-dihydro-6,7-dimethoxy-1H-2-benzopyran-1-yl)methyl]piperazine (Z)-2-butenedioate (1:2) salt. mp 200° C. The free base has an optical rotation of $[\alpha]_D^{20} = +38,5°$ (c=1, methanol).

EXAMPLE 12

In an analougous manner, as described in Example 11, but using (−)-di-O,O'-p-toluoyltartaric acid instead of (+)-di-O,O'-p-toluoyltartaric acid, (−)-1-[4,4-bis(4-fluorophenyl)butyl]-4-[(3,4-dihydro-6,7-dimethoxy-1H-2-benzopyran-1-yl)methyl]piperazine (Z)-2-butenedioate (1:2) salt was obtained. mp 198° C. The free base has an optical rotation of $[\alpha]_D^{20} = -42,2°$ (c=1, methanol).

EXAMPLE 13

1-[4,4-bis(4-fluorophenyl)butyl]-4-(3,4-dihydro-6.7-dimethoxy-1-methyl-1H-2-benzopyran-1-yl)piperidine (Z)-2-butenedioate (1:1) salt a. A mixture of 200 g of 3,4-dimethoxybenzeneethanol and 163,7 g of 1-(4-piperidinyl)ethanone in 800 ml of ethanol saturated with anhydrous hydrochloric acid was stirred for 15 h at ambient temperature. The mixture was concentrated under vacuum, and the concentrate was diluted with 500 ml of ethanol after which the hydrochloride precipitated. After filtration the hydrochloride was dissolved in water and sodium hydroxide until the pH was 12. The base was extracted with dichloromethane, and the organic phase was washed with water, dried and evaporated to yield 251 g (86,5%) of crude 4-(3,4-dihydro-6,7-dimethoxy-1-methyl-1H-2-benzopyran-1-yl)piperidine.

b. A mixture of 30 g of 4-(3,4-dihydro-6,7-dimethoxy-1-methyl-1H-2-benzopyran-1-yl)piperidine, 31,8 g of 1,1-bis(4-fluorophenyl)-4-chlorobutane and 17,1 g of potassium carbonate in 300 ml of dimethylformamide was heated at 110° C. for 1 h. Water was added and the base was extracted twice with diethyl ether, washed, dried and concentrated. The maleate was prepared in absolute ethanol to yield 46 g (68,6%) of 1-[4,4-bis-(4-fluorophenyl)butyl]-4-(3,4-dihydro-6,7-dimethoxy-1-methyl-1H-2-benzopyran-1-yl)piperidine (Z)-2-butenedioate (1:1) salt. mp 193° C.

EXAMPLE 14

In an analogous manner as described in Example 13 were prepared:

1-[2-[bis(4-fluorophenyl)methoxy]ethyl]-4-(3,4-dihydro-6,7-dimethoxy-1-methyl-1H-2-benzopyran-1-yl)piperidine (E)-2-butenedioate (1:1) salt. mp 180° C.

(−)-1-[2-[bis(4-fluorophenyl)methoxy]ethyl]-4-(3,4-dihydro-6,7-dimethoxy-1-methyl-1H-2-benzopyran-1-yl)piperidine (E)-2-butenedioate (1:1) salt. mp 149° C. $[\alpha]_D^{20} = -70,2°$ (free base, c=1, methanol).

(+)-1-[2-[bis(4-fluorophenyl)methoxy]ethyl]-4-(3,4-dihydro-6,7-dimethoxy-1-methyl-1H-2-benzopyran-1-yl)piperidine (E)-2-butenedioate (1:1) salt. mp 149° C. $[\alpha]_D^{20} = +69,2°$ (free base, c=1, methanol).

4-(3,4-dihydro-6,7-dimethoxy-1-methyl-1H-2-benzopyran-1-yl)-1-[2-(diphenylmethoxy)ethyl]piperidine (E)-2-butenedioate (1:1) salt. mp 201° C.

1-[2-[bis(4-fluorophenyl)methylthio]ethyl]-4-(3,4-dihydro-6,7-dimethoxy-1-methyl-1H-2-benzopyran-1-yl)-piperidine (E)-2-butenedioate (1:1) salt. mp 160° C.

1-[2-[bis(4-fluorophenyl)methoxy]ethyl]-4-(3,4-dihydro-6,7-dimethoxy-1H-2-benzopyran-1-yl)piperidine (E)-2-butenedioate (1:1) salt. mp 161° C.

(−)-1-[4,4-bis(4-fluorophenyl)butyl]-4-(3,4-dihydro-6,7-dimethoxy-1-methyl-1H-2-benzopyran-1-yl)piperidine (E)-2-butenedioate (1:1) salt. mp 185° C. $[\alpha]_D^{20} = -72,8°$ (free base, c=1, methanol).

(+)-1-[4,4-bis(4-fluorophenyl)butyl]-4-(3,4-dihydro-6,7-dimethoxy-1-methyl-1H-2-benzopyran-1-yl)piperidine (E)-2-butenedioate (1:1) salt. mp 159° C. $[\alpha]_D^{20} = +69,6°$ (free base, c=1, methanol).

4-(3,4-dihydro-6,7-dimethoxy-1-methyl-1H-2-benzopyran-1-yl)-1-(4,4-diphenylbutyl)piperidine (E)-2-butenedioate (1:1) salt. mp 208° C.

4-(3,4-dihydro-6,7-dimethoxy-1-methyl-1H-2-benzopyran-1-yl)-1-[3-[bis(4-fluorophenyl)methoxy]propyl]piperidine (E)-2-butenedioate (1:1) salt. mp 190° C.

We claim:

1. An isochromane derivative of the formula

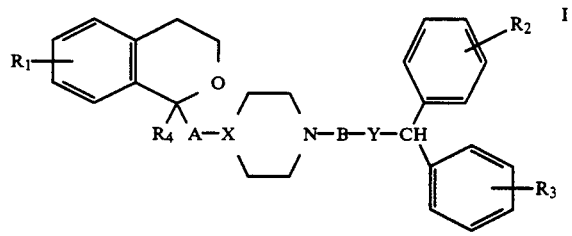

in which $R_1$ is one to four substituents independently selected from the group consisting of hydrogen, hydroxy, alkyl (1–4 C), alkoxy (1–4 C), halogen, $CF_3$ and, when $R_1$ comprises two adjacent substituents, a methylenedioxy group;

$R_2$ is one to four substituents independently selected from the group consisting of hydrogen, hydroxy, alkyl (1–4 C), alkoxy (1–4 C), halogen, $CF_3$ and, when $R_2$ comprises two adjacent substituents, a methylenedioxy group;

$R_3$ is one to four substituents independently selected from the group consisting of hydrogen, hydroxy, alkyl (1–4 C), alkoxy (1–4 C), halogen, $CF_3$ and, when $R_3$ comprises two adjacent substituents, a methylenedioxy group;

$R_4$ is selected from hydrogen or alkyl (1–4 C);

A is $CH_2$;

B is 1,3-propanediyl when Y is a bond, or B is an alkylene group with 2-6 carbon atoms when Y is selected from the group consisting of O, S and $NR_5$;

X is N; and $R_5$ is selected from hydrogen or alkyl (1-4 C); or a pharmaceutically acceptable salt thereof.

2. The isochromane derivative of claim 1, in which $R_2$ represents one, two or three methoxy groups, or a methylenedioxy group, $R_2$ and $R_3$ are hydrogen or halogen, $R_4$ is selected from hydrogen, methyl or ethyl, B is 1,3-propanediyl when Y is a bond, or B is 1,2-ethanediyl or 1,3-propanediyl when Y is, O or S, and X is N; or a pharmaceutically acceptable salt thereof.

3. The isochromane derivative of claim 2, in which $R_2$ and $R_3$ are hydrogen or para-fluorine.

4. The isochromane derivative of the formula

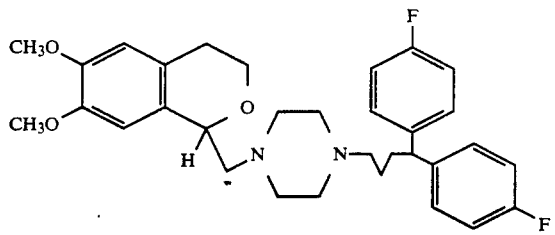

or a pharmaceutically acceptable salt thereof.

5. A pharmaceutical preparation comprising a pharmaceutically effective amount for intracellular calcium antagonist activity of the isochromane derivative of claim 1 admixed with pharmaceutically acceptable auxiliaries.

6. A method of treating angina pectoris, cardiac dysrhytmias, cardiomyopathies, stroke, or myocardial infarction comprising administering an effective amount of a compound according to claim 1.

* * * * *